United States Patent [19]
Lee

[11] Patent Number: 4,543,062
[45] Date of Patent: Sep. 24, 1985

[54] DENTAL APPARATUS AND METHOD OF USE

[76] Inventor: Robert L. Lee, 22937 Grand Terrace Rd., Colton, Calif. 92324

[21] Appl. No.: 580,071

[22] Filed: Feb. 14, 1984

[51] Int. Cl.⁴ ............................................. A61C 9/00
[52] U.S. Cl. ...................................... 433/71; 433/42; 433/214
[58] Field of Search ...................... 433/71, 37, 214, 42

[56] References Cited

U.S. PATENT DOCUMENTS

| | | | |
|---|---|---|---|
| 2,239,294 | 4/1941 | Opotow | 433/71 |
| 2,548,817 | 4/1951 | Raiche | 433/71 |
| 3,207,153 | 9/1965 | Goldstein | 433/37 |

*Primary Examiner*—Robert Peshock
*Attorney, Agent, or Firm*—Knobbe, Martens, Olson & Bear

[57] ABSTRACT

A tray for making dental check bite records is provided with a U-shaped bite section and a raised central arch. The tray is formed of stiff but deformable metal, which is perforated in the bite section to facilitate the adherence of dental impression paste. A flange on the front of the tray facilitates centering of the tray in the patient's mouth, and serrations on the edges of the tray provide convenient gripping areas when handling the tray. A check bite record is made with each tray. After first hardening an impression of the upper teeth on the tray, a glob of quicksetting impression material is positioned on the lower side of the tray to register on a lower anterior tooth. The impression in the hardened glob is then used as a pivot point to position a patient's jaw, while slower setting material is on the tray lower surface is hardening, providing an impression of the patient's lower posterior teeth in a preferred lateral position.

These check bite records are then used in combination with dental casts mounted in a dental articulator to properly set the articulator in a manner to simulate the patient's jaw movements while observing the construction of the dental cast and analyzing jaw movements. Novel selector elements are mounted in the upper frame of the articulator while using the lateral check bite records, with the selectors being used to measure lateral side shift and angular orientation. This information is utilized to select a proper set of preformed analog guide blocks to use in the articulator.

13 Claims, 14 Drawing Figures

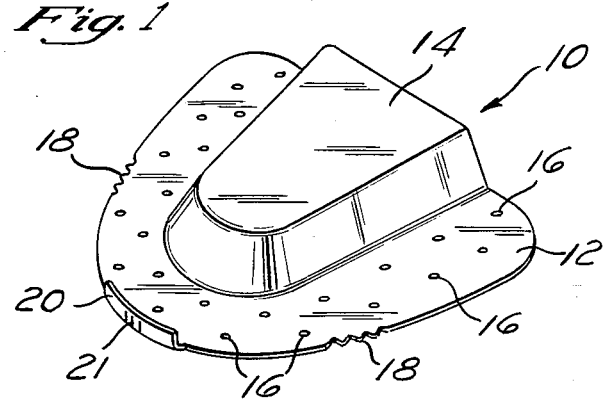
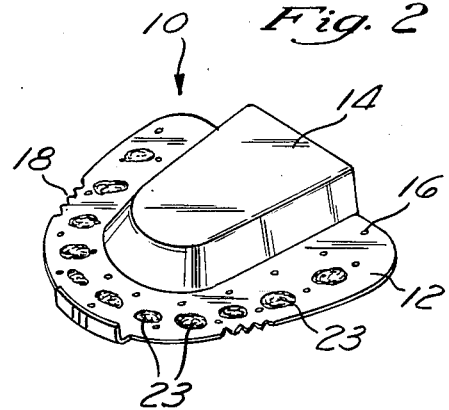
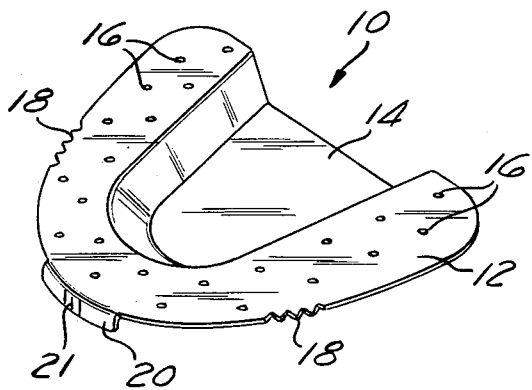
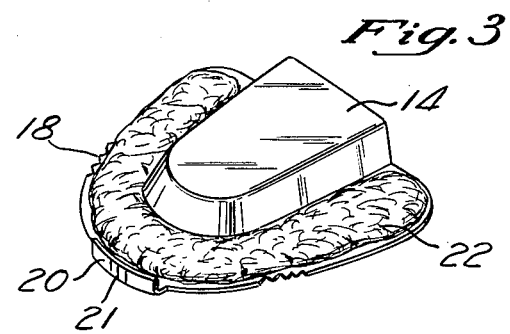
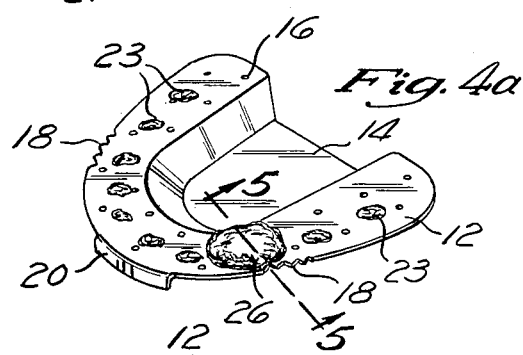
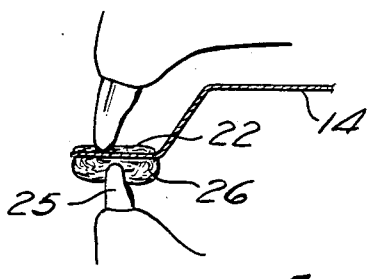
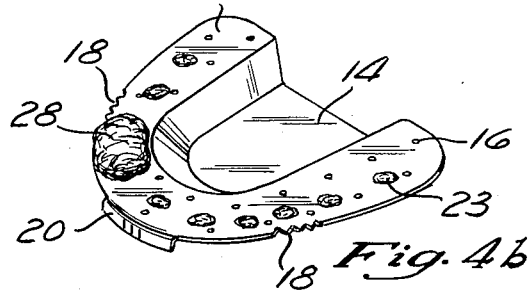
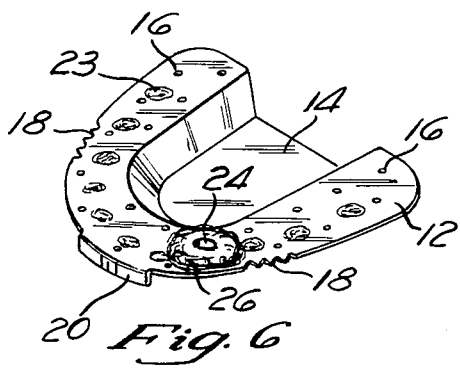
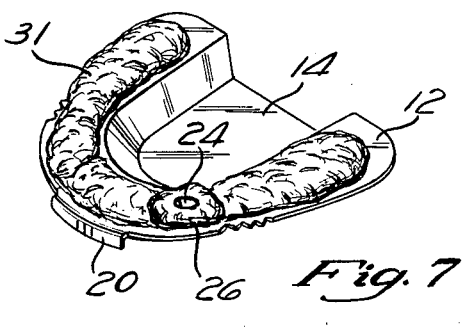

DENTAL APPARATUS AND METHOD OF USE

BACKGROUND OF THE INVENTION

This invention relates to improved apparatus and methods for use in diagnosing dental occlusions and in making and testing dental prosthetic devices outside of a patient's mouth.

The making of artificial teeth or other prosthetic devices is still, to a large extent, a trial and error technique. The desired goal is to make the necessary impressions and measurements on the patient's teeth and jaw and then make the prosthetic device and test it, without the need to see the patient until the device is ready to be fit into the patient's mouth. To accomplish this goal, one common approach is to mount the prosthetic device in a dental articulator and attempt to simulate the patient's jaw movements while observing whether the prosthetic device seems to be correctly designed. It therefore becomes necessary to be able to properly set or adjust the dental articulator so as to best simulate the patient's jaw movements.

One common technique for doing this is to make records of the patient's teeth with the jaws in various positions and then attempt to transfer the recorded information to the dental articulator. This approach is often referred to as the "checkbite" procedure wherein the patient bites into impression paste, wax or plaster, and attempts are made to maintain the patient's jaws stationary while the paste, wax or plaster sets or hardens. Simple, flat, metal sheets have been used to hold the impression material in some techniques.

This general approach is accomplished in several different ways, all of which have various advantages and disadvantages. A common advantage of this technique is that it is readily understandable and thus teachable, at least in concept, which is in contrast to some methods of making jaw measurements and setting dental articulators. On the other hand, a common disadvantage of the prior known checkbite approaches is that they are inaccurate due to improper understanding of lateral jaw movement and improper techniques, such that the mandible posterior teeth are not properly positioned when impressions are made. Further, with the methods used, it is difficult to maintain the patient's lower jaw steady while tooth impression material is hardening, and thus, difficult to obtain the desired accurate results. Thus, a need still exists for improving the apparatus and methods of simply obtaining accurate check bite records used in setting a dental articulator.

SUMMARY OF THE INVENTION

A primary component of the system of this invention is an improved check bite element for obtaining a record of the patient's jaw movements which is used for facilitating the testing of a dental prosthesis in a dental articulator. This element includes a plate or tray shaped to fit within a person's mouth between the upper and lower jaw. The tray has a generally U-shaped bite section to be positioned between the upper and lower teeth and preferably includes a raised central arch within the U-shaped bite section that fits within the arch of a person's upper jaw so as to help position the plate. The tray bite section is preferably made of a thin material which is stiff but is nevertheless deformable when clamped between the person's upper and lower teeth so that a partial impression is made of the teeth in the bite section. Preferably, the plate is stamped as a unitary element.

It is desirable that the tray bite section be formed with a plurality of perforations so that impression paste applied to the bite section will tend to be anchored thereby with the paste extending into the holes. The tray is further preferably provided with a short upwardly extending flange on its anterior edge to facilitate the proper positioning of the plate within the patient's mouth. Also, the flange may be formed with suitable markings to help center the tray in the patient's mouth and to indicate lateral movement of the lower jaw. The tray is further preferably formed with serrations or other gripping means on the side edges so as to make it easier for the operator to grip the tray when inserting or withdrawing it from the patient's mouth.

In accordance with a method of the invention, the improved check bite tray is initially inserted into the patient's mouth and the patient is instructed to bite into the tray bite section. This causes the tray material to deform somewhat making a partial impression of the patient's upper and lower teeth. The tray is then removed from the patient's mouth and dental impression material or paste is applied to the bite section of the plate. After an impression has been made and the material has hardened, a small quantity of a soft but quicksetting compound is applied to the bottom side of the tray bite section in the area of a lower tooth which is to be used as a guide in making a check bite record. For example, in making a side shift record, the compound is preferably placed in an area to be engaged by one of the lower canine teeth, and the tray is reinserted into the patient's mouth with the upper teeth in registry with the hardened impression on the upper side of the plate. The lower jaw is then shifted laterally and lightly closed so that the lower reference tooth is pressed partially into the soft but quicksetting compound. The tray is then removed; and additional impression paste is applied to the remainder of the lower surface of the bite section of the plate.

The tray is then reinserted into the mouth in registry with the upper teeth, and the jaw moved laterally into position wherein the reference tooth engages the indexing impression in the now hardened quicksetting compound. Using the hardened indexing impression as a fulcrum to support the canine teeth in a fixed selected position, the operator induces full lateral movement of the mandible by pushing laterally on the rear angular portion of the mandible. Immediatly, the condyle moves into full border movement position sometimes called "Bennett movement" or side shift. It is this position which should be recorded. In inducing such movement, the other lower teeth are, of course, pressed into the impression paste. The mandible is held in this predetermined position, guided by the hardened index until the impression paste is set, preferably, completely hardened. The tray is then removed having the desired check bite record.

A similar check bite record is then made for the side shift border movement in the opposite direction by using the other lower canine tooth as a reference point.

Using the lower incisors as reference teeth, a protrusive record may also be made, but this is not so critical in that the patient can move his jaw into the desired position. Also, a centric check bite record can be made with the use of the hardened compound, however, this is a known technique.

When the check bite reference records are to be used in setting the dental articulator, previously made dental casts of the patient's teeth are placed into a dental articulator with the centric check bite record being used in a known manner to properly position the dental casts in centric position. The lateral check bite records are then used to set the boundaries of the lateral movement of the articulator frames. To measure this movement in a manner useful in selecting appropriate analog blocks which will guide movement of the articulator frames, a special pair of measuring selector elements are mounted in the upper frame of the articulator. They are provided with an opening for receiving the styluses or condyle-like elements on the lower frame of the articulator. The guides are provided with suitable means for tracking the lateral movement of the frames when they are placed in the left and right position as determined by the check bite plates. These measurements are then utilized to select the proper guide blocks for the articulator from a supply of preformed guide blocks which are then mounted in the frame of the articulator replacing the selector elements. In this manner, the articulator is set so that the full range of movement simulating the patient's jaw movement may be obtained. These selector elements, thus, also form important components of the invention apparatus.

SUMMARY OF THE DRAWINGS

FIG. 1 is a perspective view of the top side of the check bite tray of the invention.

FIG. 2 shows the tray after it has been compressed between the patient's teeth.

FIG. 3 shows the upper surface of the tray with dental impression paste applied to the upper surface of the tray bite section.

FIG. 4 is a lower perspective view of the tray.

FIG. 4a is a perspective view of the lower side of the tray with a quantity of quicksetting compound positioned on one side of the check bite section, and FIG. 4b is a similar view showing a quantity of the compound positioned on the other side of a different check bite tray.

FIG. 5 is a schematic cross-sectional view of the tray of FIG. 4a inverted in a patient's mouth, when viewed on line 5—5, illustrating the manner the patient's lower right canine tooth is positioned in some of the quicksetting compound with the mandible shifted laterally so that the upper and lower canine teeth are approximately aligned.

FIG. 6 is a perspective view of the lower surface of the tray in FIG. 5 after an impression of the lower right canine has been made.

FIG. 7 is a perspective view of the lower surface of the tray of FIG. 6 after impression paste has been positioned on the remainder of the bite section of the lower surface of the tray.

CHECK BITE TRAY

Figure 9:
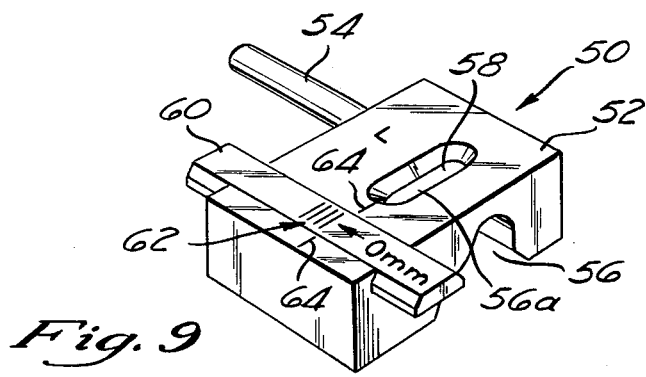
FIG. 9 is a top perspective view of a guide block element.

Referring first to FIGS. 1 and 4, the check bite element of the invention comprises a thin tray or plate 10 sized to fit within a person's mouth. The tray includes an outer U or V-shaped bite section 12 enclosing an upwardly extending arch. The bite section 12 is sized to fit between the patient's teeth while the arch mates with the arch of a person's upper jaw to properly position the plate.

Formed in the bite section 12 is a plurality of small holes or perforations 16, which facilitate the attachment of tooth impression paste to the plate. As may be seen, there is an inner and an outer U-shaped row of holes 16, with the rows being offset so that the holes in one row are midway between the holes of the other row. This arrangement provides adequate anchoring points, but minimizes the likelihood of a tooth cusp engaging a hole. Further, the holes are smaller than a tooth cusp so that a cusp cannot penetrate the tray.

Formed on the outer edge of each side of the bite section is a series of interruptions or serrations 18 which serve as means to facilitate gripping of the plate, while inserting or removing it from the patient's mouth. The ordinary tray edge is slippery and smooth such that it is difficult to hold the tray without suitable gripping means.

A short, vertically extending flange is formed on the anterior or forward edge of the central part of the bite section 12. The flange 20 extends laterally a distance about equal to the width of two or three front teeth. The forward exterior surface of the flange 20 is formed with a series of vertically extending grooves or lines 21 to serve as guides for centrally positioning the tray within a patient's mouth, and to gage mandible side shift.

The check bite tray 10 is relatively thin (preferably no more than one millimeter), being made of stiff metal which is yet sufficiently soft or malleable that it can be deformed by the patient's teeth to a limited extent when tightly gripped by the teeth. It is desirable that the material be thin and malleable so that the teeth are almost closed when impressions are made. It is, of course, necessary that the meterial employed be acceptable from a health standpoint. In one suitable example, the tray is made of dead-soft, anodized aluminum and has a thickness of about 0.5 millimeters. The tray arch serves to center the tray in the patient's mouth and also acts as a siffener for the in material. Preferably, the tray is stamped from flat stock in a multiple die operation. Stamping the tray stiffens the material in the side of the arch, while leaving the flat bite section dead-soft.

METHOD OF MAKING CHECK BITE RECORDS

In use, the check bite trays may be employed to make a record of whatever relationship between the jaws is desired. Typically, however, a check bite record is made of the jaws in centric relation position, and in the left and right extreme lateral positions. The centric relation position is that in which the mandible is centered with respect to the maxilla, and the mandible is held in its rearward-most or fully retruded position. The left and right lateral positions are those in which the lower jaw is moved laterally to its extreme left or right positions, illustrating the so-called Bennett movement or side shift. The initial steps of the procedure are the same for all of the check bite records usually made.

The tray is gripped by the thumb and index finger at the serrated edges 18, as the tray is inserted into the patient's mouth with the forward flange 20 resting against the labial surface of the incisors. The tray is centered laterally by aligning the midline mark of the lines 21 on the flange with the midline of the teeth. If the tray is too long for the patient's mouth, the rear edge may be cut with sharp scissors and the edges sanded.

The tray is then repositioned in the patient's mouth and the patient is instructed to bite down hard on the tray several times to deform it to fit closely between the teeth. When the tray is removed, it appears somewhat as illustrated in FIG. 2 with tooth impressions or indentations 23 shown in the upper surface. The tray should then be dried with compressed air and both sides of the bite section 12 painted or sprayed with a suitable material, such as a quick-drying varnish.

A small amount of zinc oxide and euginol, bite registration paste 22 is spread thinly (about 1 millimeter thick) over the upper side of the tray bite section 12. The tray is then repositioned in the patient's mouth and held in place lightly against the maxillary teeth. The patient should be instructed to tap the teeth together to assure that the tray is properly repositioned. Note that the indentations 23 made earlier assist proper alignment. The patient's mouth should then be held open slightly to keep the lower teeth away from the lower side of the tray while the operator holds the tray lightly against the upper teeth until the paste hardens.

The tray is then removed from the patient's mouth and excess material on the upper side is trimmed away with a sharp scalpel leaving only impressions of cusp tips. Loose material may be removed with compressed air. The holes or perforations 16 in the bite section 12 of the tray cause the paste to extrude into the holes to help anchor the material, and some paste flows onto the lower side of the tray. With scalpel or cotton pliers, any such excess paste that might be projecting from the lower side should be removed. The tray should then be reinserted into the patient's mouth to assure proper fit to the maxillary teeth.

The tray is then removed once more and dried with compressed air before positioning a small amount of soft, quicksetting material onto a desired portion of the lower side of the bite section of the tray. A very suitable material is the familiar dental compound, in the nature of sealing wax. This compound softens when heated but quickly hardens at room temperature. It will soften again when reheated.

For making the left and right lateral check bites, it is desirable that the glob of material be placed in an area to be contacted by a lower canine tooth on one side of the jaw. This glob is shown at 26 in FIG. 4a for one side and at 28 in FIG. 4b for the opposite side on a second tray. Although a separate tray is required for the left lateral record and for the right lateral record, the trays are numbered the same in the drawing for convenience, even though they represent different trays.

While the quicksetting material is still warm and pliable, the tray is replaced in the patient's mouth and placed in registration with the maxillary teeth. The patient should be instructed to wet with saliva the lower teeth to be engaged. The tray should be held to the upper teeth with the thumb and index finger of one hand while the thumb of the other hand holds the patient's lower lip away from the teeth. The end of the same thumb may be held against the labial surface of the lower teeth.

In making a right lateral record, the patient, with his mouth partially open, should be instructed to shift his lower jaw to the right so that the lower right canine tooth is approximately aligned with the upper right canine tooth. This is usually a lateral movement of the forward portion of the lower jaw about three millimeters. This may also be gaged by vertically aligning one of the outer lines 21 on the tray flange with the midline of the lower jaw or a spot marked on a lower incisor to indicate a three millimeter shift. The operator gradually aids the lower canine tooth 25 (FIG. 5) just contacts the soft compound 26 without the posterior teeth touching the bite tray. As soon as the canine tooth 25 touches the compound 30 and makes a light impression 24, as seen in FIG. 6, the patient should be instructed to open his mouth. After this index 24 of the lower canine tooth has been made in the compound, the tray is removed and the compound allowed to harden, which it does very quickly. The excess compound can then be cut away so that only the tip of the canine tooth can be seen (preferably no more than ½ millimeter deep in the compound).

The tray as seen in FIG. 6, should then be placed back into the patient's mouth to verify that forward portion of the mandible was shifted sideways about three millimeters when the index was formed. Marking ribbon may be used to check for the absence of contacts of the lower posterior teeth with the tray. If there is contact, more compound must be added to increase the vertical dimension and the impression steps repeated.

A thick layer (about three millimeters) of bite registration material or paste 31, as seen in FIG. 7, is then applied to the bite section 12 of the lower side of the tray and the tray is placed back into the mouth in register with the upper teeth. The mandible is then moved laterally and upwardly into position wherein the cusp of the reference canine tooth 25 fits into the index 24 in the hardened compound 26. Using the index impression as a fulcrum to support the canine tooth 25 in the fixed selected position, the operator simultaneously induces full lateral movement of the condyle area of the mandible by pushing laterally on the rear of the mandible. This immediately moves the condyle into full border or side shift movement position, which is the predetermined position desired to be recorded. The patient is instructed to hold the lower teeth in the impression paste with the lower canine 25 in the index 24 without clinching pressure until the bite paste hardens, while the operator continues to hold the rear mandible in the full side shift position. Hardening usually takes one to two minutes.

It is important to realize that the patient cannot move his jaws by himself into the desired predetermined lateral postion of full condyle border movement. If the patient were asked to move the mandible into a full lateral side shift position, the condyle area will usually tend to move in a relatively straight line forwardly and laterally, whereas with most patients, the condyle area can be shifted laterally most quickly and will move in a curved path laterally and forwardly. The patient's mandible will reach that full side shift position during certain normal chewing functions, such as while chewing dense food products, even though the patient cannot move the mandible in that manner when objects are not being chewed. This has to do with the person's chewing muscles and brain signals.

The value of the index can also be appreciated at this stage from the standpoint that the patient would not be able to hold the jaws sufficiently steady while the paste hardens without having the benefit of the index. It is important that the patient not bite hard while the registration paste is setting so that the lower jaw is being positioned solely by the index 24.

It is necessary that the paste 31 be somewhat thicker than the compound 30 between the tips of the tooth 25 and the tray bite section 12, since the lower teeth remain spaced from the tray bite section. The spots of hardened material in the holes 16 on the lower side of the tray bite section 12 help anchor the paste 31 to the tray. After the paste is set, the tray is removed from the patient's mouth and with a sharp scalpel, the excess paste is cut away on the lower side until only the cusp tips remain.

The procedure then may be repeated with another tray for a left lateral check bite record. The procedure is basically the same except that the mandible is held in the opposite side shift position or the protrusive position when the indexing or guide impression is made, and the lower canine tooth on the opposite side is used to make the record of the other lateral shift.

A protrusive check bite record may also be made by the two-step approach, using the lower incisors as the indexing teeth. However, the patient can move his jaw into the protrusive position using his jaw muscles. Thus, there is no operator induced lateral movement wherein the hardened compound is being used as a fulcrum.

A centric check bite record is needed to initially position dental casts in an articulator. Again, the lower incisors are used for indexing, but the index does not form a fulcrum for operator induced movement about the fulcrum. The operator does, however, assist in moving the mandible to its fully retruded position in making the index in the quicksetting compound. The casts of the patient's teeth that have been previously made may be checked with the registrations on the tray to see that they accurately fit into the record before mounting on an articulator. It is convenient to store the casts with the centric relation record positioned between the teeth.

Use of the two different materials and the two-step process in making the impressions on the lower teeth provides the necessary accuracy without the need for great skill. The registration paste of zinc-oxide and eugenol is excellent for making check bite records because it does not shrink and it is quite strong, but is not brittle. Also, it adheres quite well to the metal tray. It is suitable for use in a patient's mouth and is reasonably priced. Unfortunately, it does not harden quickly enough such that a patient can hold his jaw steady as the material hardens.

The sealing wax dental compound hardens quickly but it is relatively brittle and shrinks somewhat. It is suitable for indexing but not suitable for making the impression of all of the lower teeth at one time.

USE OF CHECK BITE RECORDS WITH A DENTAL ARTICULATOR

Figure 8:
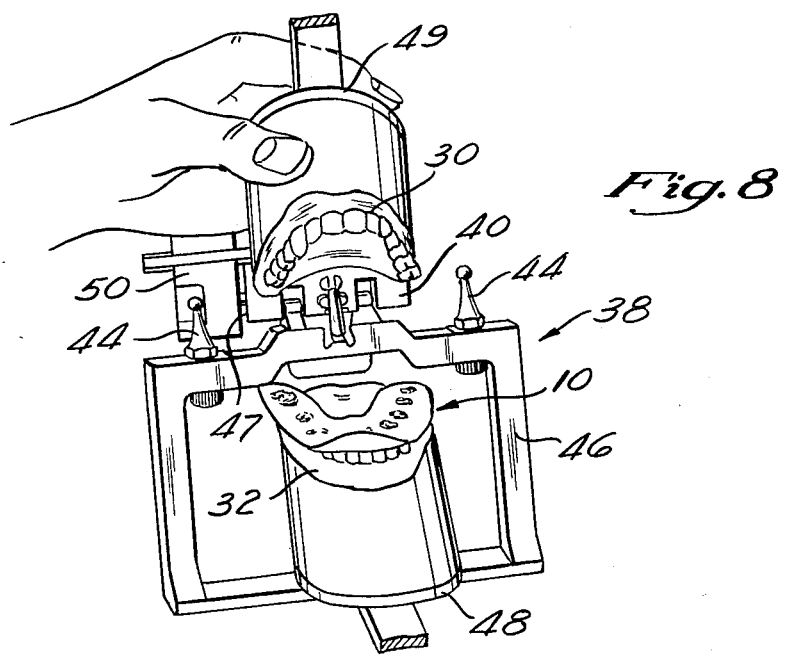
FIG. 8 is a perspective view of a dental articulator supporting a pair of dental casts, with a check bits record between them.

FIG. 8 illustrates a pair of dental casts 30 and 32 supporting a check bite record tray 10 between them. The dental casts are shown mounted in a dental articulator 38 having an upper frame 40 which support a pair of guide blocks (not shown) that cooperate with a pair of condyle-like posts or styluses 44 mounted on a lower frame 46. The frames are pivotally mounted to each other with the movement being guided by guide blocks (not shown) mounted on the upper frame which slides and pivots with respect to the styluses. Guide blocks of average value sizes are available from which operator may choose to best simulate the patient's jaw movement. These guide blocks are removably mounted in holes in the upper frame. Known means (not shown) is also provided for locking the frames to hinge only in centric position. Further details of such an articulator and such guide blocks may be seen in U.S. Pat. Nos. 4,034,474 and 4,034,475, which are incorporated herein by reference.

The dental casts 30 and 32 are shown connected by plaster to an upper mounting plate 49 and a lower mounting plate 48 which, in turn, are respectively mounted to the upper and lower articulator frames 40 and 46.

The purpose of mounting the dental casts 30 and 32 in the articulator is to enable the operator to move the articulator frames in a manner to simulate the movement of the patient's jaw movement so as to observe the movement and the fit between the artificial teeth. This procedure minimizes the time required to actually fit the artificial teeth in the patient's mouth. The purpose of the check bite records is to position the dental casts in the border positions in the articulator so that guide blocks of the desired type may be selected to provide movement within the limits determined by the check bite records. The centric check bite record is used in a known manner in properly mounting the dental casts to their mounting plates. The dental casts, while gripping the centric check bite record, are supported for a suitable fixture (not shown) between the upper and lower articulator frames. The casts are then plastered to the mounting plates 47 and 48, while the plates are fixed to the articulator.

Figure 10:
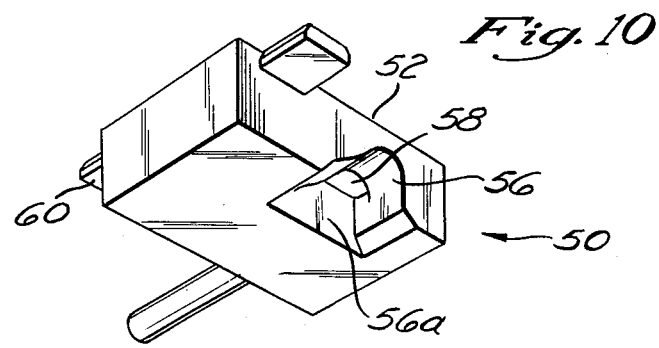
FIG. 10 is a bottom perspective view of the selector of FIG. 9.

The lateral check bite records are then used to hold the articulator frames in the lateral position. To assist in the process of determining which guide blocks to select, there is provided a pair of guide block selectors which replace the guide blocks when the check bite records are being used. Such a guide block selector 50 is shown in FIGS. 9 and 10. The left selector is shown for purposes of illustration, but the right selector is the same, only reversed. The numbers refer to either a right or a left selector. As may be seen, the selector 50 includes a small, generally rectangular block-like body or element 52, connected to a mounting pin 54 that mounts in the dental articulator in the same hole in which a guide block is mounted when the articulator is being used to simulate jaw movement. In the lower surface of the element, there is provided an opening 56 for receiving a stylus 44 on the lower frame of the articulator. A slot 58 in the upper wall of the element 52 opens into the opening 56 in the lower surface of the element. The elongated slot 58 extends generally perpendicular to the pin 54, with the left inner edge of the slot, as viewed in FIG. 9, being flush with the inner or medial wall 56a of the opening 56.

Also formed in the upper surface of the selector element 52 is a horizontally extending groove in which is slidably positioned a horizontally movable pin 60, which may be referred to as a Bennett scale, inasmuch it is used to measure side or lateral movement. Small calibration lines 62 are formed on the upper side of the Bennett scale, generally perpendicular to the mounting pin 54 and alignable with a reference line 64 on the adjacent upper surface of the selector element. This line 64 is in the same vertical plane as the medial wall 56a.

As indicated above, the analog selectors are used with the lateral check bite records. As shown in FIG. 8, the guide blocks have been removed from the upper frame of the artculator and the right analog selector 50 is mounted in the right side of the upper frame of the articulator. Note that left and right refer to the orientation that it would be for the patient. Thus, if the dental casts shown in FIG. 8 were assumed to be in a patient's mouth, the right side of the patient's jaw, as viewed from the patient's perspective, is where the right analog selector is positioned. From the perspective of the viewer in FIG. 8, the right analog selector is on the left. The selector 50 should be transversely positioned, initially, against the calibrated side 47 of the upper frame 40 of the articulator. The selector should be rotated to its maximum upper position so that the walls of the selector opening 56 are not engaging the stylus 44. The set screw 55 (FIG. 11) is then tightened against the mounting pin 54 to hold the selector in that position.

The centric check bite record has been removed and replaced by the left lateral check bite record being carefully positioned onto the lower dental cast 32. Note that the left check bite record is used with the right selector 50 so as to obtain the best balance. The upper frame 40 of the articulator is then carefully lowered to register the teeth of the upper dental cast 30 with the tooth impressions in the upper surface of the check bite plate. Assuming that the patient had some left lateral movement, it will be necessary to laterally slide the upper frame of the articulator a slight amount and probably move it forwardly so that the upper teeth will align properly.

With the upper dental cast firmly positioned into the check bite record, there will be space between the stylus or condyle 44 and the walls of the opening 56 in the analog selector 50. While pressing the maxillary cast firmly downward into the check bite, the mounting screw 55 holding the selector pin 54 should be loosened allowing the selector to pivot downward to contact the upper surface of the stylus.

Figure 11:
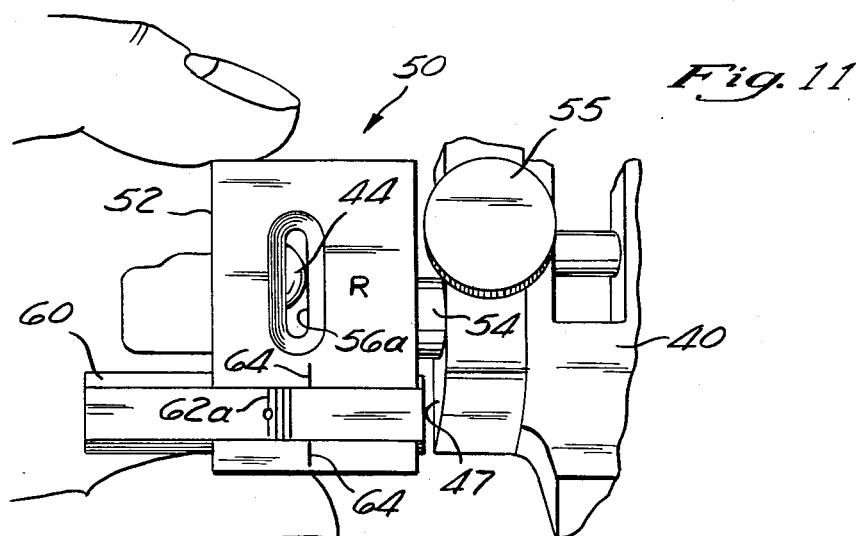
FIG. 11 is a fragmentary perspective view of the right selector mounted in the articulator and engaging the medial side of the condylar element.

The selector 50 should then be pulled outwardly, laterally so that the medial wall 56a of the selector opening 56 engages the medial side of the stylus 44. This condition is shown in FIG. 11. The selector 50 is locked in this position by tightening the thumb screw 55 against the mounting pin 54.

Figure 12:
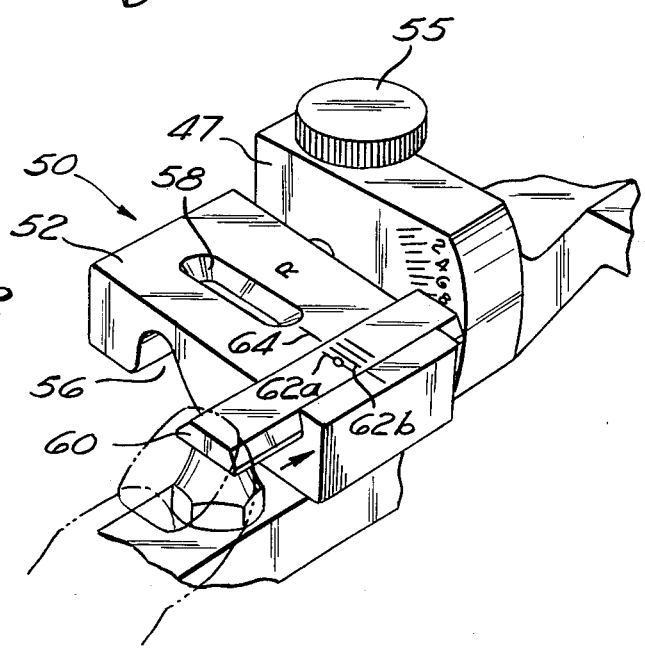
FIG. 12 is a fragmentary perspective view illustrating the Bennett scale being manipulated to provide a reading of side shift measurement and angular orientation.

The Bennett scale 60 is then pushed inwardly or medially until it touches the calibrated side 47 of the articulator frame 40, as shown in FIG. 12. The amount of Bennett movement is read in millimeters on the small scale 62. If the scale line 62a on the extreme left is aligned with the reference line 64 on the upper surface of the selector, there would be zero side shift. The line 62a may be provided with a zero marked thereon to facilitate observation. For the patient in FIG. 12, the second scale line 62b is aligned with the reference line 64. This indicates that the patient has one millimeter of Bennett or lateral side movement. Therefore, a preformed analog or guide block having a one millimeter side shift capacity is to be used on this side of the articulated frame to guide the movement of the upper frame with respect to the lower frame. As indicated above, the analog block is selected from a supply of blocks having preformed openings of various sizes.

The desired angular inclination for the selected analog guide block is read by observing where the end of the Bennett scale 60 touches the calibrated side 47 of the articulator frame 40. For the teeth of the patient illustrated, this appears to be an angular inclination reading of about 7. Thus, when the selector 50 is removed and replaced by an analog guide block, the block is similarly oriented to the number 7 position. The upper surface of the selector has the same relation to its mounting pin as does the guide block to its mounting pin.

The above procedure is then repeated to select the left side analog. That is, the left side selector 50 shown in FIG. 10 is mounted in the upper articulator frame engaging the other calibrated side of the frame 40, and the patient's right lateral check bite record is positioned between the dental casts. It should be recognized that the patient's left and right lateral movements are not necessarily the same and thus the left side might require a side shift greater than the other, for example. This completes the selection process and the operator can now proceed with the movement of the articulator frames to simulate the patient's jaw movements, and thereby test the adequacy of the dental casts.

It should be noted that while there are many steps to the procedure of making the check bite records and utilizing them to set the articulator frames, the steps are all relatively simple and require little judgment on the part of the operator. This is of great significance in that it enables an operator to be quickly trained, and enables personnel other than dentists to perform the procedures. Related to this, the apparatus and supplies required are relatively inexpensive. That is, the check bite trays are mass produced with the desired shape and configuration. The impression paste and the quick setting materials are also relatively inexpensive. While the precision made left and right selector elements introduce some expense, only a single set is required, since they are usuable for all patients.

I claim:

1. A dental check bite element for making a record of a patient's bite, such record facilitating the mounting od dental prosthesis in a dental articulator, said element comprising a tray shaped to fit within a person's mouth between the upper and lower jaws, the tray including a generally thin, U-shaped bite section to be positioned between the upper and lower teeth, and including a raised central arch within the U-shaped bite section to fit within the arch of the person's upper jaw, the tray bite section being made of stiff material which is deformable when clamped between the person's upper and lower teeth in the bite section; the central forward portion of the bite section including a short upwardly extending flange on the anterior edge; and means formed on the lateral edges of said tray to facilitate gripping the tray when inserting or removing the tray from a patient's mouth.

2. The element of claim 1 wherein the plate arch is also made of said thin, stiff material.

3. The element of claim 1 including indicia formed on said flange to aid in centrally positioning the tray with respect to the person's upper teeth.

4. The element of claim 1 including indicia formed on the flange to indicate lateral positions of the lower jaw.

5. The element of claim 1 including indicia formed on the anterior portion of the bite section indicating the center of the tray and predetermined location on either side of the center.

6. The element of claim 1 wherein said bite section is flat except for said anterior flange.

7. The element of claim 1 including serrations formed in the lateral edges of the tray to facilitate gripping the tray when inserting or removing its from a patient's mouth.

8. The element of claim 1 wherein said tray is made of anodized aluminum and is less than one millimeter thick.

9. The element of claim 1, wherein said bite section is formed with a plurality of holes therethrough to facilitate the attachment of tooth impression material to the tray.

10. The element of claim 1, wherein the means for gripping the tray are in the area of the bite section to be engaged by the patient's bicuspids.

11. A dental check bite element comprising a tray shaped to fit within a person's mouth between the upper and lower teeth, the tray including a peripheral bite section to be engaged by the upper and lower teeth, a layer of impression material adhered to the upper surface of the bite section with an impression of the patient's upper teeth being formed in the impression material when it is hardened, a quantity of quicksetting compound, having a more rapid set-up time than said impression material, attached to the lower surface of the tray having an index impression formed therein of a patient's lower tooth with the lower jaw in a first predetermined eccentric lateral position with respect to the upper jaw, and a layer of impression material adhered to the lower surface of the bite section with an impression of the patient's lower teeth formed therein when the lower jaw is in a second predetermined lateral position and the tooth that made the index impression is in the index impression, whereby a check bite record of the patient's teeth is made with the lower jaw in said second lateral position.

12. The element of claim 11 wherein said impression of said lower teeth is made when the rear area of said lower jaw is in its left or right border lateral position, and the index impression is made by utilizing one lower canine tooth area for making an index impression for one lateral position or using the other lower canine tooth area for making an index impression for the other lateral position.

13. A dental check bite element comprising a thin metal tray shaped to fit within a person's mouth between the upper and lower teeth, the tray including a generally U-shaped bite section to be engaged by the upper and lower teeth and having a raised, central arch between the bite section to fit within the arch of a person's upper jaw so as to aid in positioning the tray, the tray material being stiff but deformable when clamped between the person's upper and lower teeth so that a partial impression is made of the teeth in the bite section, the bite section having a plurality of holes formed therethrough for facilitating the attachment of impression paste to the bite section, the central forward portion of the bite section including a short, upwardly extending, flange on its anterior edge with indicia formed on the anterior surface of the flange for facilitating the central positioning of the tray within the patient's mouth, and the bite section including gripping serrations on each lateral edge to facilitate gripping the tray when it is being inserted or withdrawn from a patient's mouth.

* * * * *